(12) United States Patent
Chan et al.

(10) Patent No.: US 6,215,403 B1
(45) Date of Patent: Apr. 10, 2001

(54) WIRELESS MONITORING SYSTEM

(75) Inventors: Hoi Yeung Chan, Stamford, CT (US); Thomas Yu-Kiu Kwok, Washington Township, NJ (US); Fred Tze-Keung Tong, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/238,537

(22) Filed: Jan. 27, 1999

(51) Int. Cl.[7] .................................................. G08B 23/00
(52) U.S. Cl. .............................. 340/573.1; 340/670.18; 600/323; 600/479; 600/481; 600/483
(58) Field of Search .......................... 340/573.1, 870.18; 600/300, 323, 328, 504, 341, 481, 479, 483

(56) References Cited

U.S. PATENT DOCUMENTS

| | | | |
|---|---|---|---|
| 3,925,762 | * 12/1975 | Heitlinger et al. | 340/573.1 |
| 4,890,619 | * 1/1990 | Hatschek | 600/323 |
| 5,153,584 | * 10/1992 | Engira | 340/870.18 |
| 5,203,342 | * 4/1993 | Sakai | 600/504 |
| 5,299,570 | * 4/1994 | Hatschek | 600/479 |
| 5,647,359 | * 7/1997 | Kohno et al. | 600/341 |
| 5,724,025 | * 3/1998 | Tavori | 340/573.1 |
| 5,779,631 | * 7/1998 | Chance | 600/328 |
| 5,964,701 | * 10/1999 | Asada et al. | 600/300 |

FOREIGN PATENT DOCUMENTS

| | | |
|---|---|---|
| 0553372 | 8/1993 | (EP) . |
| 0770349 | 5/1997 | (EP) . |
| 2686497 | 7/1993 | (FR) . |

* cited by examiner

Primary Examiner—Benjamin C. Lee
(74) Attorney, Agent, or Firm—F. Chau & Associates, LLP

(57) ABSTRACT

In accordance with the present invention, a detection device capable of being coupled to a person for remotely monitoring heart and respiratory functions includes a processor, a photo cell coupled to the processor for determining blood oxygen content of the person and a temperature sensor coupled to the processor for determining a temperature of the person. The processor compares the determined blood oxygen content and the temperature to desired values. A transmitter is included for transmitting a warning signal if one of the determined blood oxygen content and the temperature are other than the desired values.

14 Claims, 5 Drawing Sheets

WIRELESS MONITORING SYSTEM

BACKGROUND OF THE INVENTION

1. Field of the Invention

The present invention relates to a wireless monitoring system and more particularly to a suffocation prevention system, temperature monitor system and indoor communication systems.

2. Description of the Related Art

Every year thousands of babies die of premature crib death, also known as Sudden Infant Death Syndrome. While some of them inherited some problems such as heart irregularities or respiratory distress, other deaths are caused by accidents such as suffocation from blankets or pillows and lack of attention to certain readily observable conditions such as body temperature due to illness. In almost all cases, early detection can save the infants from death. Even though the probability of such tragedies happening is relatively small, most parents and caretakers are eager to acquire a device that will help them to further minimize the chance of suffocation if the device is inexpensive and easy to use. For example, the sales of carbon monoxide detectors can best illustrate the motive.

Therefore, a need exists for providing a system for early warning to allow quick response to signs of suffocation in infants or other people who are unable to help themselves. Such a system could save thousands of lives every year. A further need exists for early detection of progressing illness which may relieve parents or caretakers some of the stress and effort in monitoring people under their care.

SUMMARY OF THE INVENTION

In accordance with the present invention, a detection device capable of being coupled to a person for remotely monitoring heart and respiratory functions includes a processor, a photo cell coupled to the processor for determining blood oxygen content of the person and a temperature sensor coupled to the processor for determining a temperature of the person. The processor compares the determined blood oxygen content and the temperature to desired values. A transmitter is included for transmitting a warning signal if one of the determined blood oxygen content and the temperature are other than the desired values.

A system for remotely monitoring heart and respiratory functions includes a detection device capable of being coupled to a person including a processor, a photo cell coupled to the processor for determining blood oxygen content of the person, a temperature sensor coupled to the processor for determining a temperature of the person. The processor compares the determined blood oxygen content and the temperature to desired values. A transmitter is included for transmitting a warning signal if one of the determined blood oxygen content and the temperature are other than the desired values. A receiver capable of being remotely coupled to the transmitter to receive the warning signal is also included.

Another system for remotely monitoring heart and respiratory functions includes a plurality of detection devices each capable of being coupled to a different person, the detection devices including, a processor, a photo cell coupled to the processor for determining blood oxygen content of the person and a temperature sensor coupled to the processor for determining a temperature of the person. The processor compares the determined blood oxygen content and the temperature to desired values. A transmitter is included for transmitting a warning signal if one of the determined blood oxygen content and the temperature are other than the desired values, the warning signal having uniquely identifying characteristics to identify each different person being monitored. A receiver is also included capable of being remotely coupled to the transmitters to receive the warning signals with uniquely identifying characteristics, the receiver capable of taking appropriate actions based on each person identified by the warning signals.

In alternate embodiments, the detection device preferably includes a power source for powering the detection device. The power source preferably includes a battery. The transmitter(s) may transmit radio frequency signals. The desired levels may include a predetermined blood oxygen content level and a predetermined temperature range. The desired levels may also include previous blood oxygen content readings and previous temperature readings. The receiver may include a warning system for alerting users of the warning signal. The warning system may include one of a flashing light, a speaker, a beeper and a telephone. The warning signals may include RFID signals. The receiver may include a server having a database for storing information about people wearing the detection devices. The information about people wearing the detection devices includes appropriate actions to be taken upon receiving the warning signals.

These and other objects, features and advantages of the present invention will become apparent from the following detailed description of illustrative embodiments thereof, which is to be read in connection with the accompanying drawings.

BRIEF DESCRIPTION OF DRAWINGS

The invention will be described in detail in the following description of preferred embodiments with reference to the following figures wherein.

DETAILED DESCRIPTION OF PREFERRED EMBODIMENTS

The present invention relates to a wireless monitoring system and more particularly to a suffocation prevention system, temperature monitor system and indoor communication system. The present invention provides a remote monitoring system which provides reliable monitoring of blood oxygen levels and temperature to ensure proper breathing to infants and bed-ridden individuals who need monitoring. If oxygen levels or temperature in the individual drop below a predetermined level, an alarm or other warning signal is activated to provide an early response to the situation.

Figure 1:
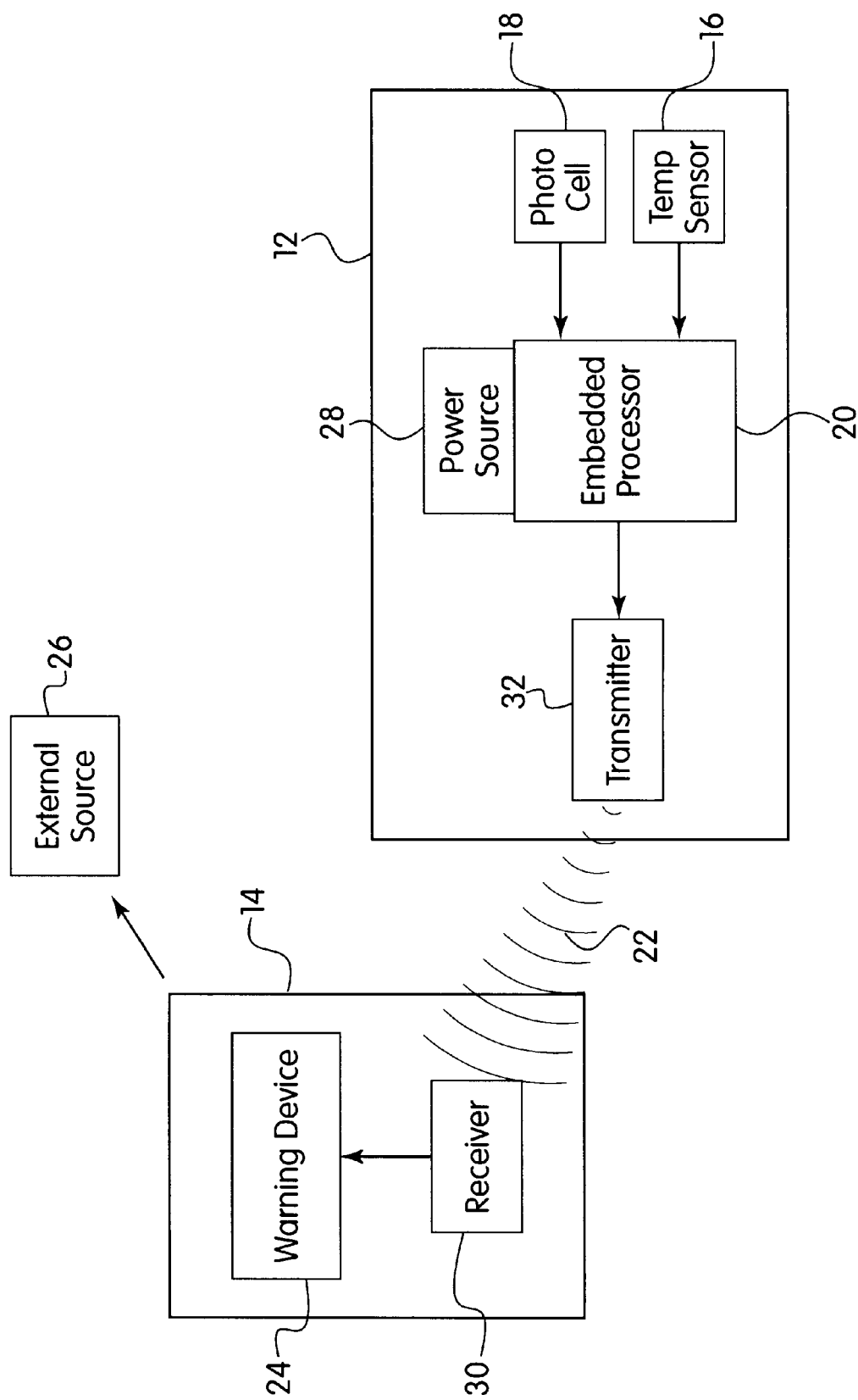
FIG. 1 is a block diagram showing a wireless monitoring system in accordance with one embodiment of the present invention showing a sensor/transmitter and a warning system receiver in accordance with the present invention.

Referring now to the drawings in which like numerals represent the same or similar elements and initially to FIG. 1, a schematic diagram showing a wireless system 10 in accordance with the present invention. System 10 includes a sensor/transmitter 12 and a warning system/receiver 14. Sensor/transmitter 12 includes a temperature sensor 16 which may include a detector for measuring emitted radiation, such as infrared radiation from a body of a user, or a thermocouple to continuously measure the body temperature. A photocell 18 detects the oxygen level of the user. This is preferably performed by measuring the difference between oxi-hemoglobin and dioxide hemoglobin. Normally, the level of oxygen in the blood is 100%, but if it falls below 100%, a signal output by photocell 18 will change according to the difference. The oxi-hemoglobin and dioxide hemoglobin levels are measured according to the wavelength of light emitted from the body of the user. Red wavelengths indicate blood is well oxygenated while bluer wavelengths indicate an oxygen deficiency. Photocell 18 receives the radiation from the body and preferably utilizes the photo-electric or equivalent effects to generate an electrical output signal.

The output signals from temperature sensor 16 and photocell 18 are sent to an embedded processor 20 for processing. Processor 20 may include a microprocessor having one or more semiconductor chips or may include hard wired circuits with the capabilities described below. Processor 20 processes the signals from the photocell 18 and temperature sensor 16. These signals may be filtered and compared to a previous oxygen level and temperature or compared to predetermined oxygen levels and temperature ranges. If the oxygen level is lower than the predetermined value or the temperature measured is out of range then processor 20 sends a signal 22, preferably, a Radio Frequency (RF) signal through a transmitter 32, preferably an RF transmitter, to warning system/receiver 14. A receiver 30 receives RF signal 22 and activates an alarm or warning device 24. Warning device 24 may include a beeper, a telephone system, a walkie talkie, or similar device. Warning device 24 may include a flashing light, a warning buzzer from a speaker or other devices. In a preferred embodiment, alarm device includes the capability to make an emergency call to an external source 26 such as an ambulance, doctor, or other emergency service.

Sensor/transmitter 12 and warning system/receiver 14 may be located in close proximity or far apart depending on the signals used to implement the devices. Further, although described in terms of RF other signals may be employed such as infrared, etc. Sensor/transmitter 12 includes a power source 28 preferably a portable power source such as a battery, a solar cell or equivalents. Power source 28 may include non-portable sources as well, such as electrical power from an outlet. Sensor/transmitter 12 may include an additional warning feature to indicate a low battery, for example.

Figure 2:
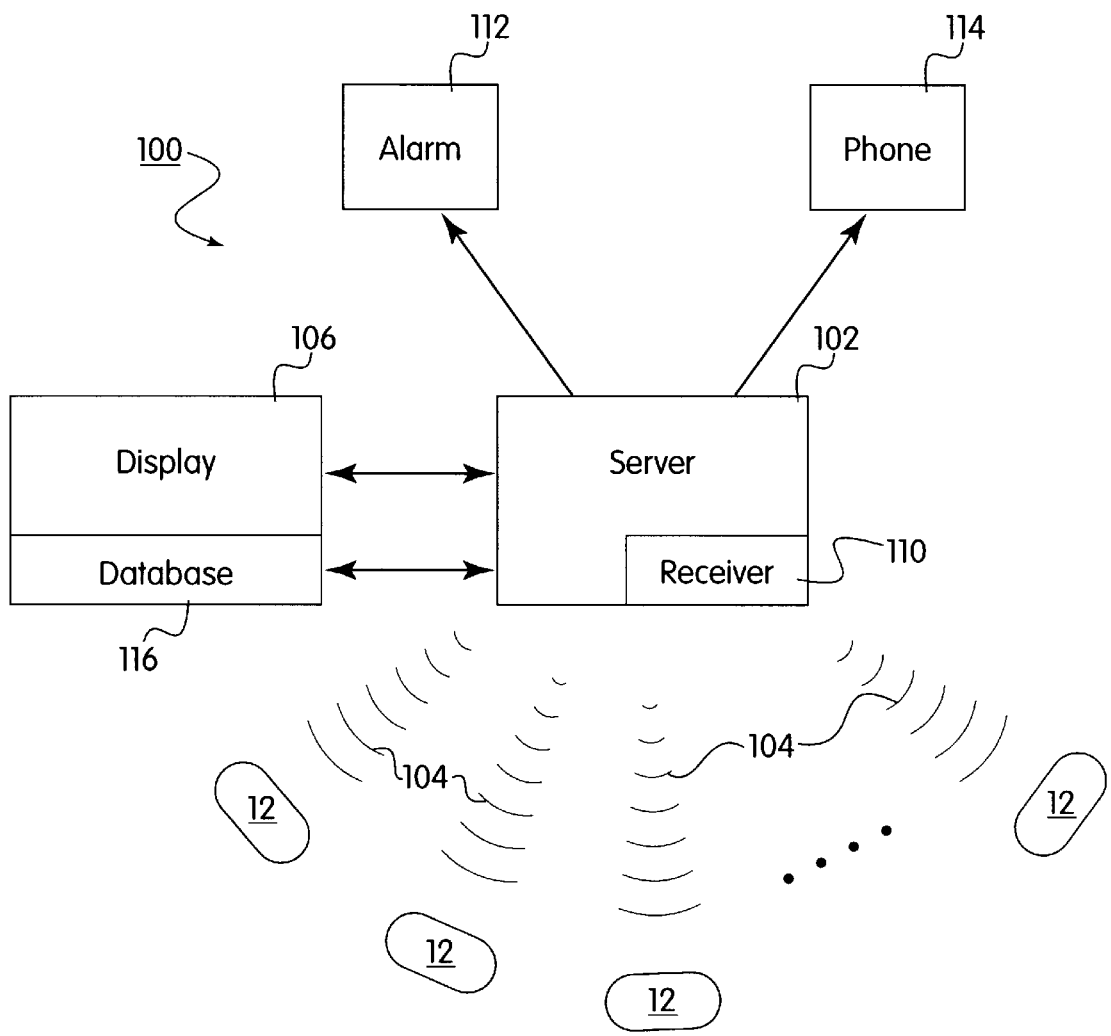
FIG. 2 is a block diagram showing a wireless monitoring system for a plurality of sensor/transmitters in accordance with another embodiment of the present invention.

Referring to FIG. 2, in one embodiment, a system 100 is provided for use in an environment such as a hospital or ward. System 100 is employed to handle a plurality of sensor/transmitters 12. A centralized server 102 is included to serve many clients simultaneously. Centralized server 102 functions similarly as warning system/receiver 14. However, centralized server 102 receives an identifying signal 104 from each of sensor/transmitters 12. Identifying signals 104 are preferably RF signals, which may be modulated to uniquely identify each identifying signal. Each signal may be made unique by employing a different frequency, employing a different wavelength, employing a different synchronization, etc. for the signal. If identifying signals 104 are digital, identifying signals 104 may be encoded and decoded differently or include an encryption code or a digital key to differentiate between the signals to identify different patients.

In a preferred embodiment, identifying signals 104 are transmitted from sensor/transmitters 12 when the monitored conditions fall below a threshold value or are out of range. Identifying signals 104 may further provide specific information about the patient and the conditions being monitored such as temperature and blood oxygen content. Centralized server 102 includes a receiver 110 for receiving the identifying signals. Centralized server 102 may include a processor and a database 116 for formatting and outputting data received for sensor/transmitters 12 and to maintain a log of the conditions being monitored along with time information, such as when an alarm was activated. A display 106 may be included for displaying the data received according to each patient.

Centralized server 102 receives an identifying signal and takes appropriate actions. This may include activation of an alarm 112, warning device (beeper, etc.) or dialing a phone 114 to call for help from an external source, as described above.

Figure 3:
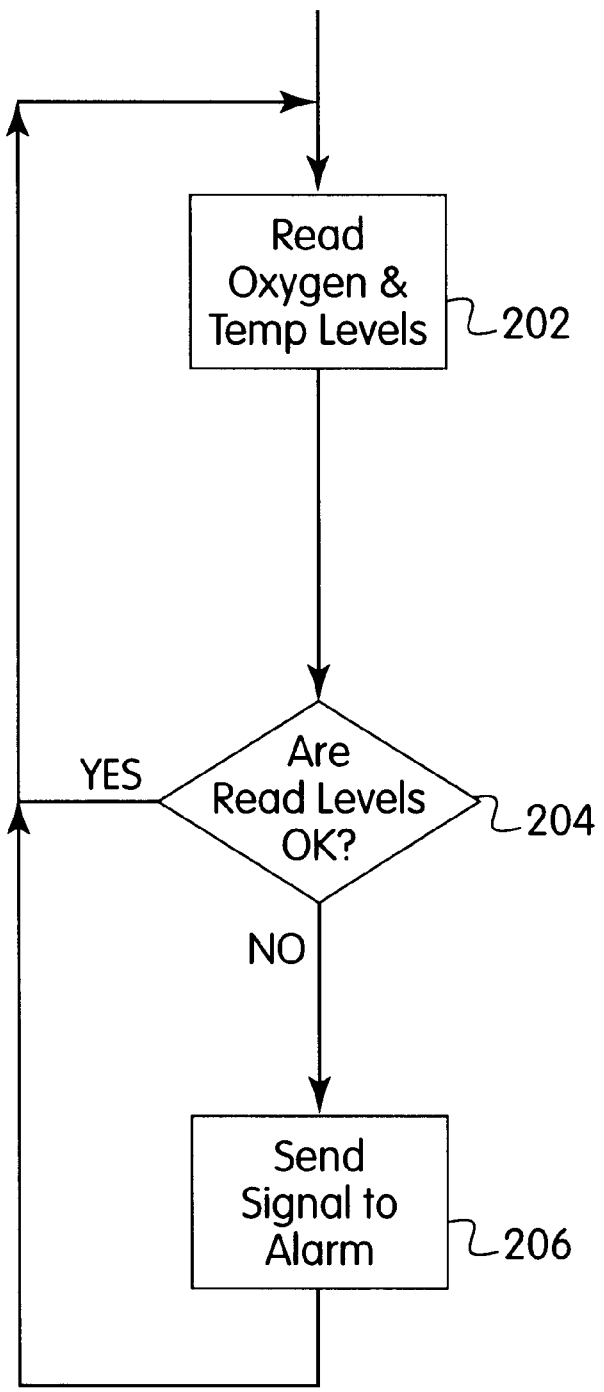
FIG. 3 is a flow diagram for a method of monitoring blood oxygen content and temperature in accordance with the present invention.

Referring now to FIG. 3, a method for monitoring a patient or infant is shown. Processor 20 is used to monitor the patient or infant and performs the method shown in FIG. 3. In step 202, oxygen levels are read from photo sensor 18, and temperature levels are read from temperature sensor 16 (FIG. 1). In step 204, the oxygen levels and the temperature reading are compared to preset levels. This may be performed using Boolean logic, an adder circuit or other devices known in the art. In an alternative embodiment, current levels of oxygen and/or temperature are compared to a previous set of readings to determine changes between the readings. If the temperature readings are out of range or the oxygen levels are below the preset levels, a signal is sent to a warning device by employing a transmitter in step 206. Otherwise, the oxygen level and the temperature of the patient will be monitored by returning to step 202. This method continues until a warning is activated or the system is turned off.

Figure 4:
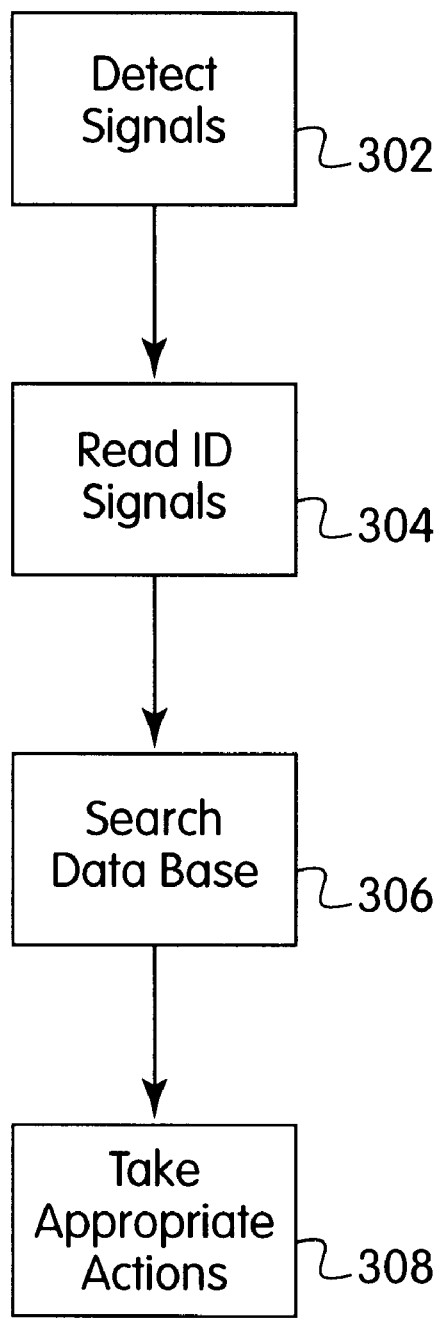
FIG. 4 is a flow diagram for a method for monitoring identifying signals and taking appropriate actions in accordance with the present invention.

Referring to FIG. 4, a method for employing centralized server 102 used when detecting identifying signals is shown. Centralized server 102 detects signals from sensor/transmitters 12 in step 302. In step 304, the identifying signals from sensor/transmitters 12 are read or processed. In step 306, a data base search may be performed to correlate the identifying signal, for example, an RFID signal to a patient and/or a patients information such as room number, name, etc. The data base may be included in the centralized server 102. The data base may also include appropriate action messages which the person monitoring the system may take, for example, "call doctor" or more specifically "call Doctor Smith at 555-5555". Other messages are also contemplated. In step 308, appropriate actions are taken, such as setting alarms, displaying alert messages in a display, calling via phone an emergency number, etc. Each action taken is preferably responsive to the particular individual uniquely identified by the identifying signal.

Figure 5:
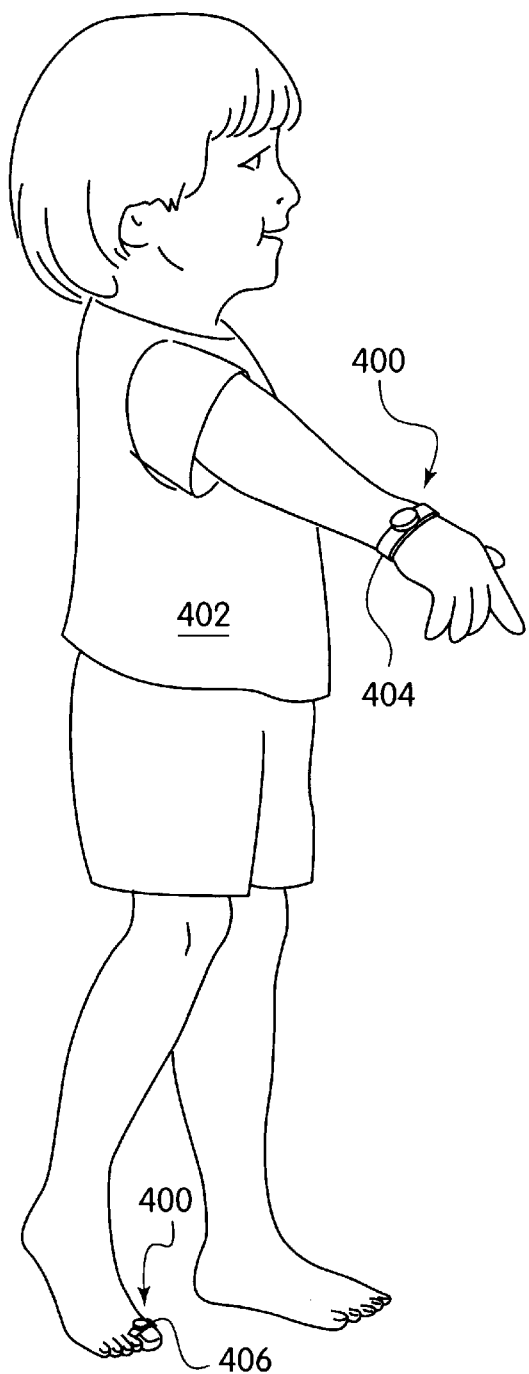
FIG. 5 is a perspective view of a person wearing detection devices in accordance with the present invention.
Figure 6:
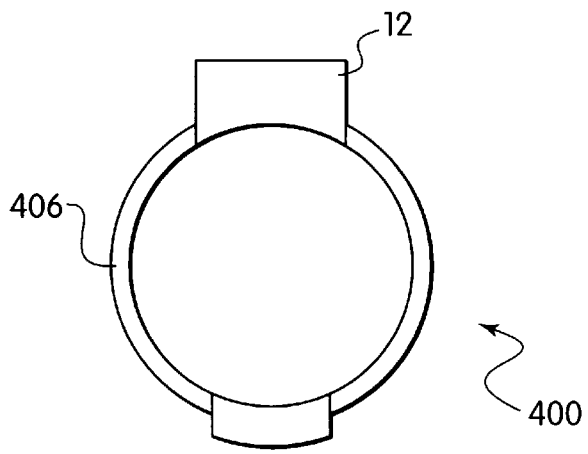
FIG. 6 is a side view of a detection device with an adjustable strap in accordance with the present invention.

Referring to FIGS. 5 and 6, the present invention includes a detection device 400 including sensor/transmitter 12 that detects heart or respiratory problems by examining the oxygen level in the blood of a person 402 such as an infant and/or a temperature sensor that measures the temperature of the person continuously. This device 400 may be attached to a person's wrist (in the form of a bracelet 404) or attached to a toe or leg with an adjustable strap 406 or the like. A signal will be sent from device 400 to an embedded processor 20 which is integrated in device 400. When processor 20 detects an abnormal condition, processor 20 will activate transmitter 32 to send an RF wireless signal to a warning system/receiver 14 to alert the parents or the caretakers of the baby, child or adult.

Having described preferred embodiments of a wireless monitoring system (which are intended to be illustrative and not limiting), it is noted that modifications and variations can be made by persons skilled in the art in light of the above teachings. It is therefore to be understood that changes may be made in the particular embodiments of the invention disclosed which are within the scope and spirit of the invention as outlined by the appended claims. Having thus described the invention with the details and particularity required by the patent laws, what is claimed and desired protected by Letters Patent is set forth in the appended claims.

What is claimed is:

1. A system for remotely monitoring heart and respiratory functions comprising:
   a detection device capable of being coupled to a person comprising:
   a processor;
   a photo cell coupled to the processor for determining blood oxygen content of the person;
   a temperature sensor coupled to the processor for determining a temperature of the person;
   the processor for comparing the determined blood oxygen content and the temperature to desired values, wherein the desired levels include previous blood oxygen content readings and previous temperature readings; and
   a transmitter for transmitting a warning signal if one of the determined blood oxygen content and the temperature are other than the desired values; and
   a receiver capable of being remotely coupled to the transmitter to receive the warning signal, the receiver including a capability for calling a predetermined external source by telephone; and
   the receiver includes a warning system for alerting users of the warning signal with at least one of a beeper and a telephone.

2. The system as recited in claim 1, wherein the detection device further comprises a power source for powering the detection device.

3. The system as recited in claim 2, wherein the power source includes a battery.

4. The system as recited in claim 3, wherein the transmitter transmits radio frequency signals.

5. The system as recited in claim 1, wherein the desired levels include a predetermined blood oxygen content level and a predetermined temperature range.

6. A system for remotely monitoring heart and respiratory functions comprising:
   a plurality of detection devices each capable of being coupled to a different person, the detection devices comprising:
   a processor;
   a photo cell coupled to the processor for determining blood oxygen content of the person;
   a temperature sensor coupled to the processor for determining a temperature of the person;
   the processor for comparing the determined blood oxygen content and the temperature to desired values; and
   a transmitter for transmitting a warning signal if one of the determined blood oxygen content and the temperature are other than the desired values, the warning signal having uniquely identifying characteristics to identify each different person being monitored;
   a receiver capable of being remotely coupled to the transmitters to receive the warning signals with uniquely identifying characteristics, the receiver capable of taking appropriate actions based on each person identified by the warning signals including a capability for calling a predetermined external source by telephone; and
   the receiver includes a warning system for alerting users of the warning signal with at least one of a beeper and a telephone.

7. The system as recited in claim 6, wherein the detection device further comprises a power source for powering the detection device.

8. The system as recited in claim 6, wherein the power source includes a battery.

9. The system as recited in claim 8, wherein the transmitters transmit radio frequency signals.

10. The system as recited in claim 6, wherein the desired levels include a predetermined blood oxygen content level and a predetermined temperature range.

11. The system as recited in claim 6, wherein the desired levels include previous blood oxygen content readings and previous temperature readings.

12. The system as recited in claim 6, wherein the warning signals include RFID signals.

13. The system as recited in claim 6, wherein the receiver includes a server having a database for storing information about people wearing the detection devices.

14. The system as recited in claim 13, wherein the information about people wearing the detection devices includes appropriate actions to be taken upon receiving the warning signals.

* * * * *